(12) United States Patent
Richards et al.

(10) Patent No.: US 8,225,785 B2
(45) Date of Patent: Jul. 24, 2012

(54) VIBRATORY PEP THERAPY SYSTEM WITH MEDICATED AEROSOL NEBULIZER

(75) Inventors: Fredrick M. Richards, Clinton, NY (US); Robert R. Cianfrocco, Rome, NY (US)

(73) Assignee: Smiths Medical ASD, Inc., Keene, NH (US)

( * ) Notice: Subject to any disclaimer, the term of this patent is extended or adjusted under 35 U.S.C. 154(b) by 1668 days.

(21) Appl. No.: 11/538,329

(22) Filed: Oct. 3, 2006

(65) Prior Publication Data

US 2008/0078383 A1  Apr. 3, 2008

(51) Int. Cl.
*A61M 16/00*  (2006.01)
*A62B 9/00*  (2006.01)
*A62B 9/02*  (2006.01)
*A63B 23/18*  (2006.01)
*A61B 5/08*  (2006.01)

(52) U.S. Cl. ......... 128/204.12; 128/204.18; 128/204.19; 128/205.23; 128/205.24; 482/13; 137/908; 600/538; 600/540

(58) Field of Classification Search ............. 128/204.18, 128/204.19, 205.24, 205.23; 482/13; 137/908; 600/538, 540
See application file for complete search history.

(56) References Cited

U.S. PATENT DOCUMENTS

| | | | |
|---|---|---|---|
| 5,086,765 A * | 2/1992 | Levine ................... | 128/200.21 |
| 6,412,481 B1 * | 7/2002 | Bienvenu et al. ........ | 128/200.21 |
| 6,581,598 B1 | 6/2003 | Foran et al. | |
| 6,776,159 B2 * | 8/2004 | Pelerossi et al. ......... | 128/204.18 |
| 2003/0209247 A1 | 11/2003 | O'Rourke | |

FOREIGN PATENT DOCUMENTS

| EP | 1435251 | 7/2004 |
|---|---|---|
| EP | 1464357 | 10/2004 |

* cited by examiner

*Primary Examiner* — Patricia Bianco
*Assistant Examiner* — Nihir Patel
(74) *Attorney, Agent, or Firm* — Luedeka Neely Group, P.C.

(57) ABSTRACT

A positive oscillatory expiratory air pressure respiratory therapy device which is adapted to receive a nebulizer for administering aerosolized medicant for selective administration during oscillatory positive expiratory pressure (PEP) therapy.

4 Claims, 7 Drawing Sheets

VIBRATORY PEP THERAPY SYSTEM WITH MEDICATED AEROSOL NEBULIZER

FIELD

This invention relates to the field of respiratory therapy, and, more particularly, to a single patient use positive oscillatory expiratory pressure respiratory therapy device adapted for use with a medicated aerosol drug delivery system to administer positive expiratory pressure therapy (PEP).

BACKGROUND

Persons who suffer from mucus-producing respiratory conditions that result in large amounts of mucus being produced in the lungs often require assistance in the removal of these secretions. If these secretions are allowed to remain in the lungs, airway obstruction occurs resulting in poor oxygenation and possible pneumonia and/or death. One of the clinically recognized treatments for this condition is a technique known as positive expiratory pressure therapy or PEP. With PEP therapy, a patient exhales against a resistance to generate expiratory pressure at a substantially constant rate of flow. Prescribed expiratory pressures are generally in the range of 10-20 cm of $H_2O$, although other pressure ranges and pressures can be used, with a preferred flow rate of between 10-25 liters per minute.

In the use of PEP therapy, a patient breaths through an orifice restrictor to generate a positive pressure in the lungs during exhalation, with the pressure falling to zero at the end of the exhalation. By selection of the proper-sized orifice, a given pressure is determined for the exhalation flow rate generated by an individual patient. This extended, substantially constant, flow of elevated-pressure exhalation has been shown to be effective for moving secretions trapped in the lungs to the larger airways where the secretions can then be removed through coughing. It has also been found that in the treatment of patients having chronic obstructive pulmonary disease (COPD), chronic bronchitis, cystic fibrosis, atelectasis, or other conditions producing retained secretions, treatment with PEP therapy is improved by combining positive expiratory pressure therapy with airway oscillation and intermittent air-flow acceleration. To this end hand-held, single patient multi-use, positive expiratory pressure respiratory therapy devices have been developed such as those of U.S. Pat. No. 6,581,598, "POSITIVE EXPIRATORY PRESSURE DEVICE", and U.S. Pat. No. 7,059,324, "POSITIVE EXPIRATORY PRESSURE DEVICE".

The devices of the referenced patents have accomplished their desired objectives, and, accordingly, it has become desirable to incorporate such PEP and COPD therapies with a medicated aerosol drug delivery system.

SUMMARY

The present invention is directed to overcoming one or more of the problems or disadvantages associated with the relevant technology. As will be more readily understood and fully appreciated from the following detailed description of a preferred embodiment, the present invention is embodied in a positive oscillatory expiratory air pressure respiratory therapy device which includes a medicated aerosol nebulizer for the selective administration of medicated oscillatory PEP therapy.

BRIEF DESCRIPTION OF THE DRAWINGS

Further advantages of the invention, together with additional features contributing thereto and advantages accruing therefrom, will be apparent by reference to the following detailed description of a preferred embodiment of the invention which is shown in conjunction with the accompanying drawings, which are not to scale so as to more clearly show the details, wherein like reference numbers indicate corresponding parts and like elements throughout the several views, wherein.

DETAILED DESCRIPTION OF THE INVENTION

Figure 1:
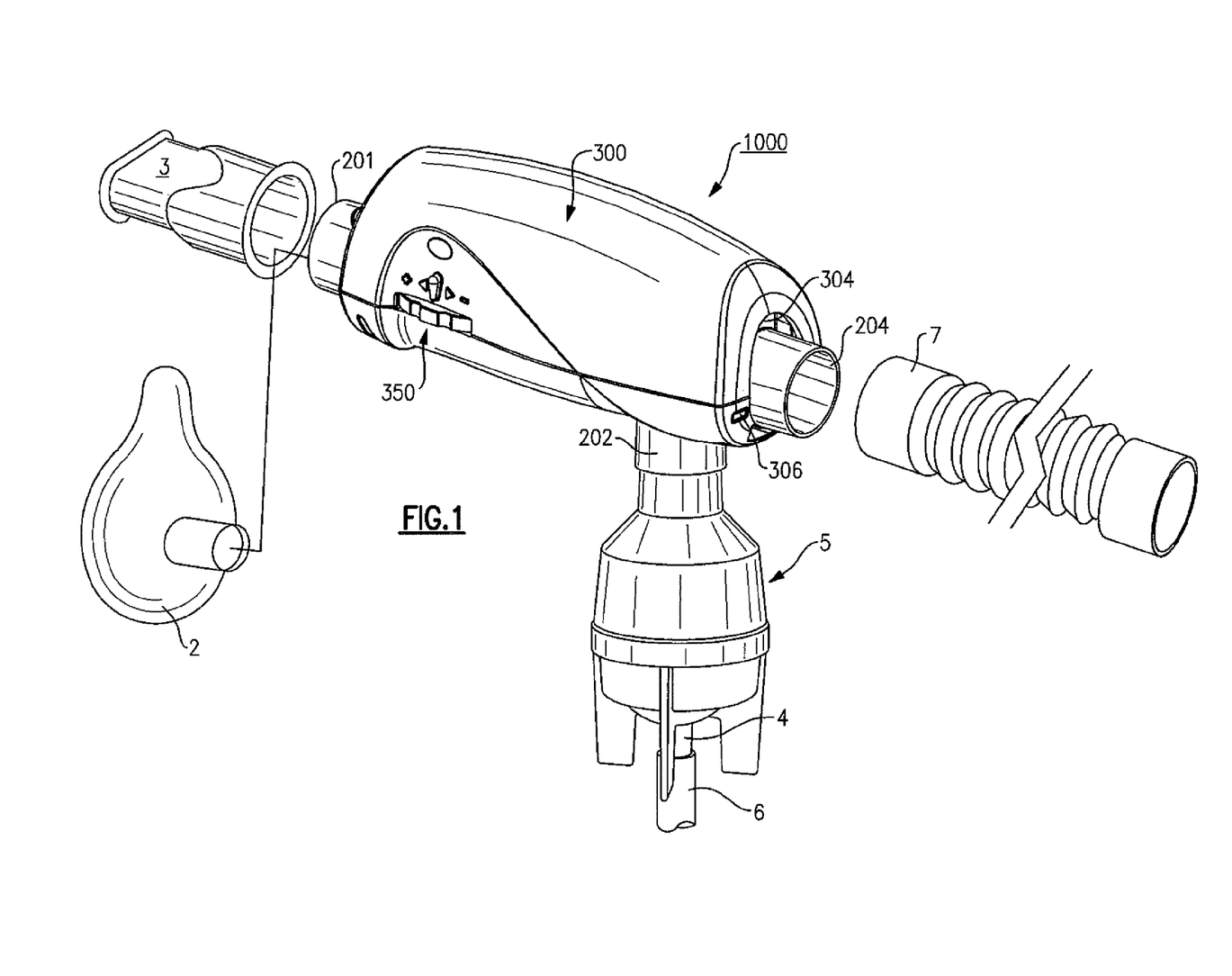
FIG. 1 is a perspective view of an embodiment of the invention in a suitable environment.
Figure 2:
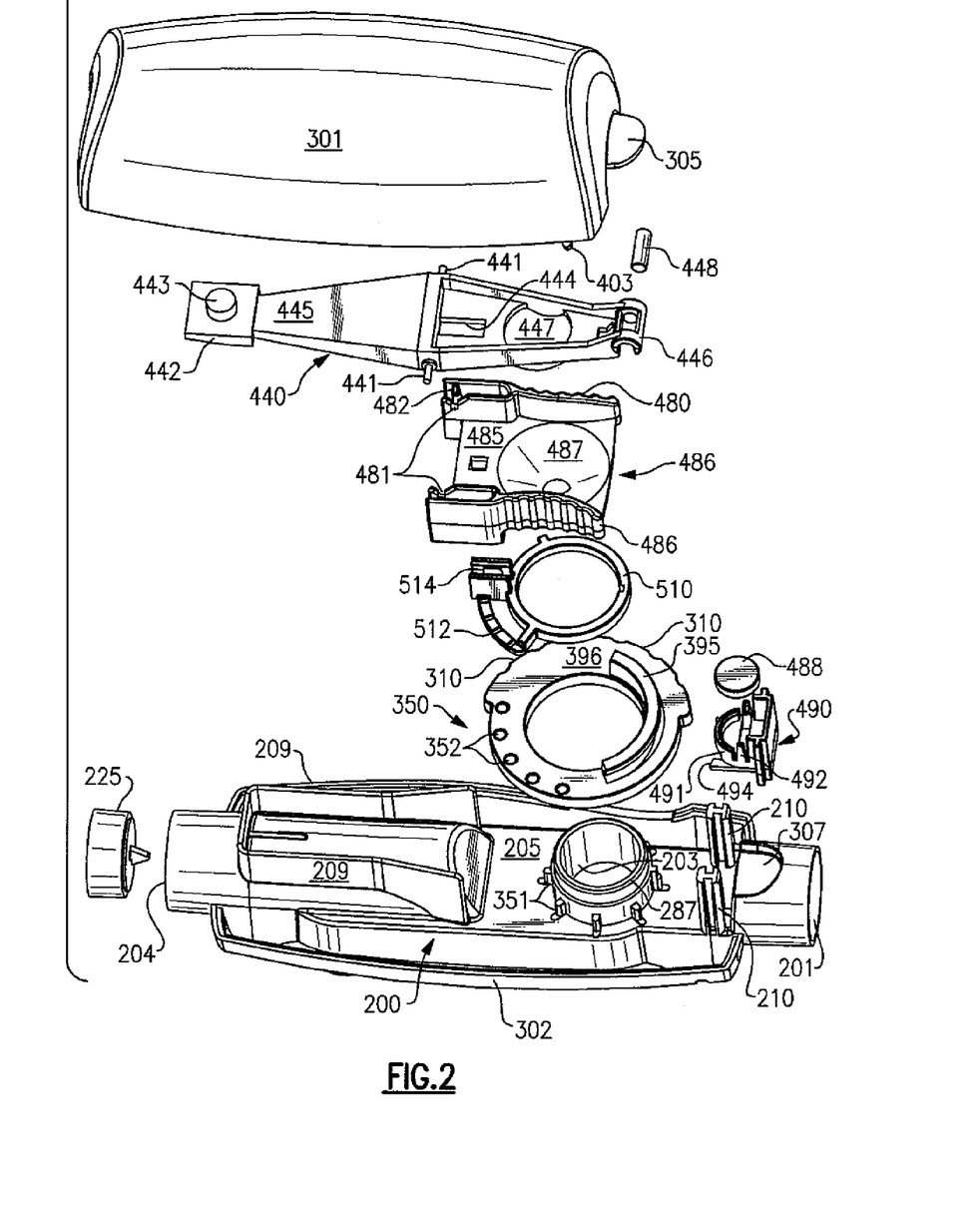
FIG. 2 is an exploded perspective view of the embodiment illustrated in FIG. 1 with portions removed to better illustrate the internal structure thereof.
Figure 3:
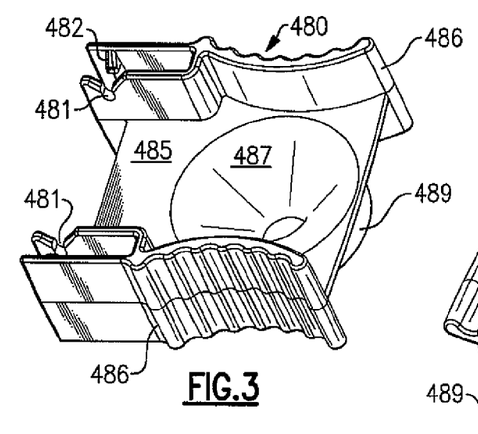
FIGS. 3, 4, 5 and 6 are, respectively, an upper and lower perspective view, top elevation and sectional view of a platform portion of the embodiment illustrated in FIG. 1 to better illustrate a portion of the structure forming a non-linear discharge orifice.
Figure 4:
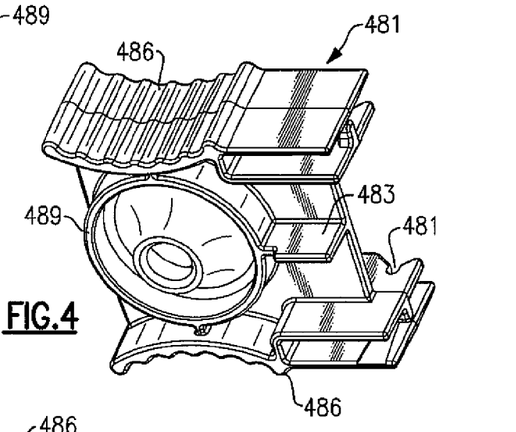
Figure 5:
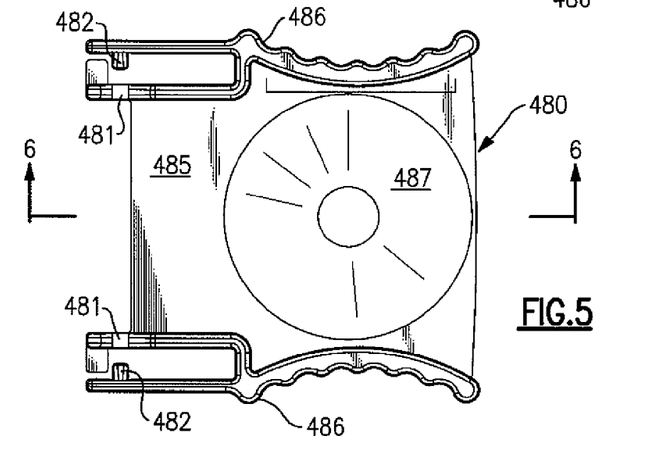
Figure 6:
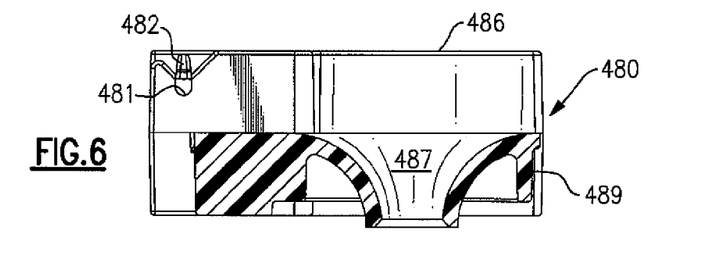
Figure 7:
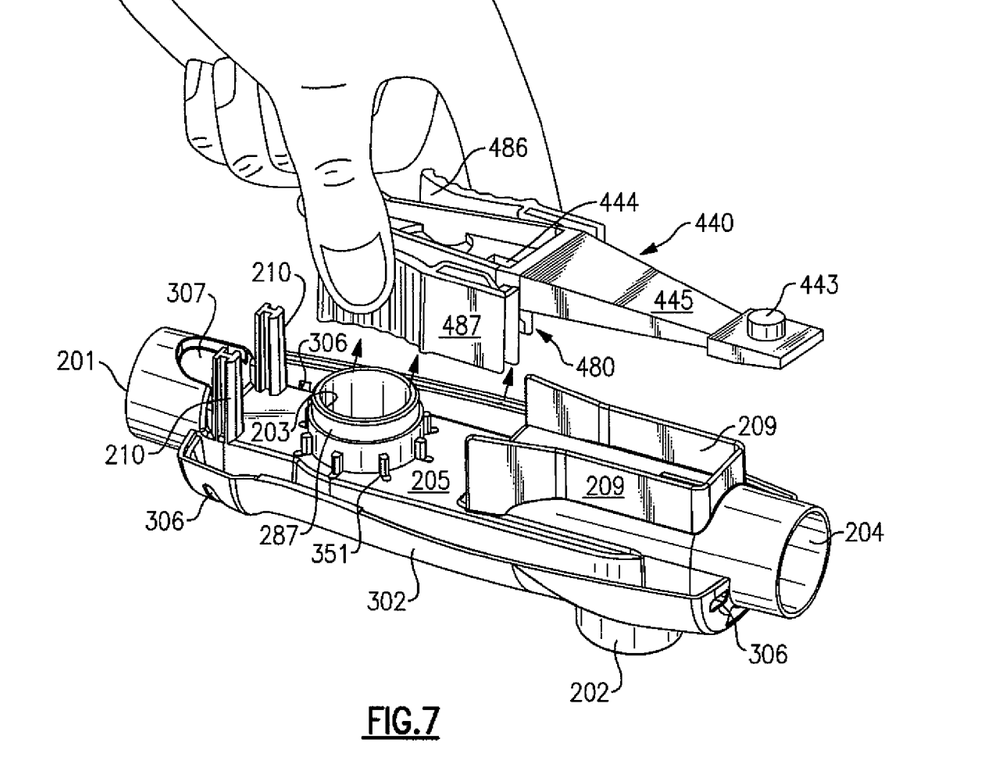
FIG. 7 is a perspective view of rocker and platform portions of the embodiment illustrated in FIG. 1 with parts removed as these portions are installed onto a lower portion of the device housing for producing an oscillatory positive expiratory air pressure.
Figure 8:
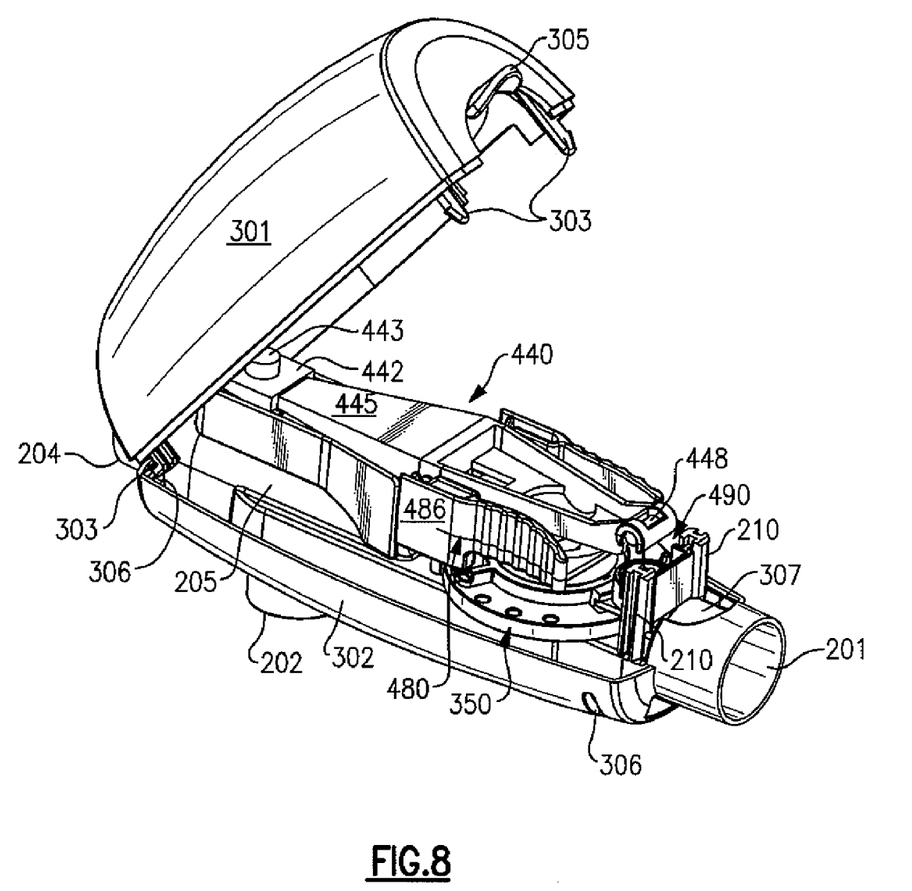
FIG. 8 is a perspective view of an assembled oscillatory positive expiratory pressure device with the upper portion of the device open to better illustrate a portion of the structure for adjusting the magnitude and frequency of the oscillatory positive expiratory air pressure and the ease in which the device may be disassembled and assembled for cleaning.
Figure 9:
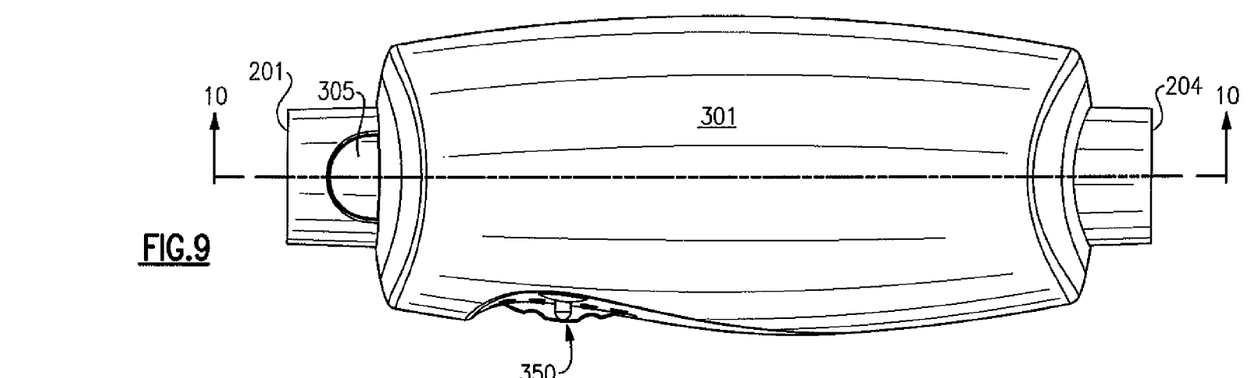
FIG. 9 is a top elevation view of the assembled oscillatory positive expiratory pressure producing device.
Figure 10:
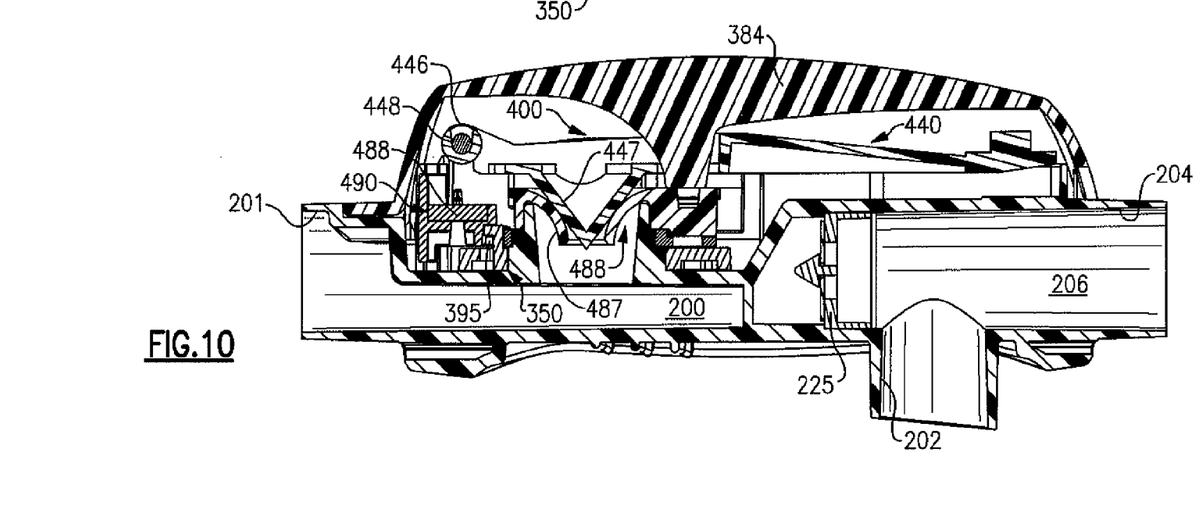
FIG. 10 is a sectional view of the oscillatory positive expiratory pressure device as illustrated in FIG. 9 taken along lines 10-10 to better illustrate the internal structure for creating the oscillatory positive expiratory air pressure and to control the oscillatory frequency and pressure, and the manner in which the magnitude and frequency of the oscillations can be varied.
Figure 11:
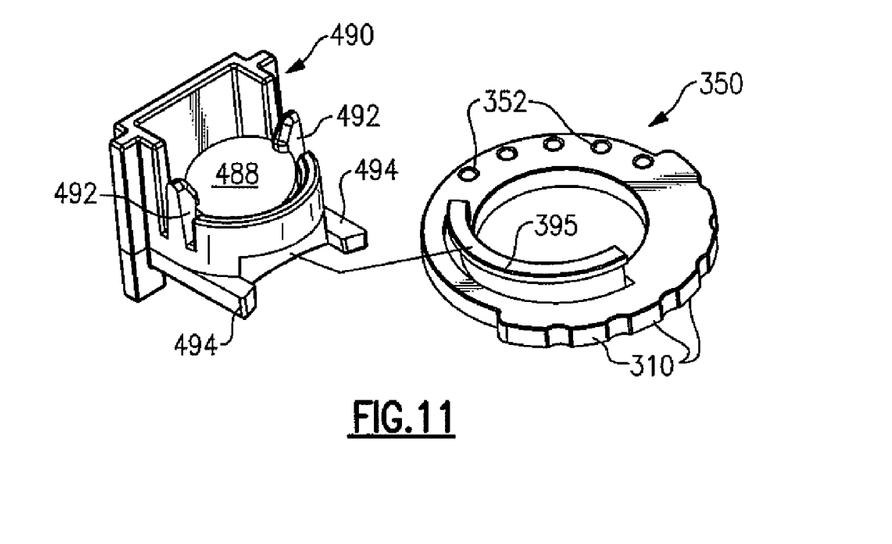
FIG. 11 is a perspective view of an adjustable dial portion of the oscillatory positive expiratory pressure device to better illustrate the manner in which a magnetic coupling and magnet holder are positionable relative to the rocker portion illustrated in FIG. 2 to set the magnitude and frequency of the oscillations.
Figure 12:
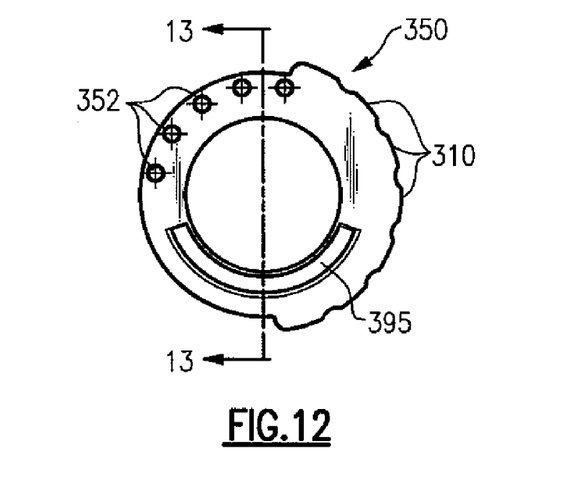
FIG. 12 is a planar view of the adjustment dial illustrated in FIG. 11 to better illustrate the structure and function thereof.
Figure 13:
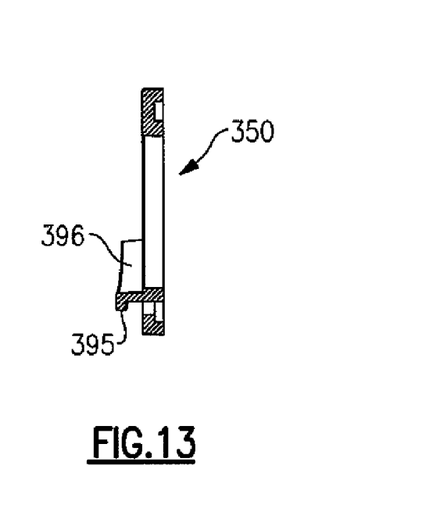
FIG. 13 is a sectional view of the adjustment dial taken along lines 13-13.

Referring now to the drawings, there is illustrated in FIGS. 1 and 2 an oscillatory positive expiratory pressure (PEP) respiratory therapy device 1000 for applying oscillatory positive expiratory air pressure therapy to a patient to which medicated aerosolized drugs are administered by means of a small volume nebulizer 5.

The oscillatory PEP device 1000 is coupled in fluid communication to the nebulizer 5 which functions to supply aerosolized medicine and/or humidified gas to the patient and may be used by the patient with a standard 22 mm removable mouthpiece 3 or a 22 mm standard mask 2. Oxygen and/or other gases to be supplied to the patient, as determined by a clinician, are coupled to the nebulizer 5 through a tubing 6 connected at one end to a suitable fitting 4 on the base of the nebulizer 5, and at another end to the desired gas source (not shown). If desired, as determined by the clinician, medication can be added to the nebulizer 5 for administration to the patient. The nebulizer 5 is coupled to the oscillatory PEP device 1000 through a nebulizer input port 202 on the underside of the PEP device 1000 so that the desired gases and medicine are supplied to the patient, preferably at a rate between about 5 to about 7 liters per minute.

The patient inhales deeply through a patient coupling port 201 to which, for convenience of illustration, the removable mouth piece 3 is connected to enable the patient to inhale at a rate and to an extent as determined by the clinician. Inspiratory air enters the PEP device 1000 through an inspiratory air port 204. If desired, reservoir tubing 7 may be attached to the inlet port 204. A one-way valve 225 is positioned in the inlet air chamber 206 of the PEP device downstream of the inspiratory air port 204 and the nebulizer input port 202 so that inspiratory air may freely enter the device through the valve 225, but expiratory air from the patient is blocked from being expelled through the inspiratory air port 204 or back into the nebulizer 5.

Expiratory air is passed from the patient through the mouthpiece 3 and out through the patient coupling port 201 into the oscillatory PEP device 1000. The expiratory air passes through the patient coupling port 201 into and through an air-flow tube 200 to an expiratory-air-driven oscillatory rocker assembly 400 contained within a two part housing 300. The expiratory-air-driven oscillatory rocker assembly 400 creates an oscillatory positive expiratory air pressure (PEP) which is applied to the patient during exhalation. The expiratory-air-driven oscillatory rocker assembly 400 comprises two portions, a rocker portion 440 and a rocker support or platform portion 480 which act together in creating the oscillatory PEP therapy. It is preferable that the patient maintain exhalation for about 3 to about 4 seconds.

To control the magnitude and frequency of the oscillatory pressure applied to the patient, a rotatable frequency control dial 350 is carried in a horizontal position about a discharge opening 203 of the air-flow tube 200, the conduit which receives the expiratory air from a patient which is passed through the patient coupling port 201. The air-flow tube 200 is carried by a lower housing portion 302, and supports the expiratory-air-driven oscillatory rocker assembly 400. By operation of the adjustable frequency control dial 350, the relative positioning between the oscillatory PEP inducing portions of the oscillatory rocker assembly 400, the rocker portion 440 and the rocker support portion 480, are adjusted to control or set the magnitude and frequency of the oscillatory expiratory air pressure.

The expiratory-air-driven oscillatory rocker portion 440 is best illustrated in the exploded view of FIG. 2 and FIGS. 7, 8 and 10. The rocker support portion 480, which functions in cooperation with the rocker portion 440 to produce an oscillatory expiratory air flow and pressure, is also illustrated in the exploded view of FIG. 2, and in more detail in FIGS. 7, 8 and 10. The expiratory-air-driven oscillatory rocker portion 440 and the rocker support portion 480, when assembled together, form the rocker assembly 400.

The rocker assembly 400 is supported on the air-flow tube 200 which has at one end the inspiratory air port 204 through which inspiratory air is received by the patient by means of the one-way valve 225, and at another end a discharge opening 203 through which expiratory air from the patient is passed to the rocker assembly 400 to produce the oscillatory expiratory air flow and pressure. The air-flow tube discharge opening 203 is formed on a top flat planar surface portion 205 of the air-flow tube 200 and the expiratory air passed there through is applied to the oscillatory rocker assembly 400 for creating the oscillatory PEP therapy for the patient. After the expiratory air has been applied to the oscillatory rocker assembly 400 to create the desired oscillatory waveform, the air thereafter exits from the device 1000 through an exit opening 304 formed by a spacing between the upper and lower portions 301 and 302, respectively, of the housing 300 at an end opposite to the patient coupling port 201.

As best illustrated in FIGS. 2, 7, 8 and 10, the rocker portion 440 is balanced for pivotal movement about pivot pins 441 on spaced pivot supports 481 formed on a platform 485 of the rocker support portion 480. The pivot pins 441 form a pivot axis transverse to the plane of motion of the rocker portion 440 and lie in a plane above and extending transverse to the longitudinal axis of the platform 485 upon which the rocker portion 440 is supported. The pivot pins 441 engage a pair of locking guides 482 carried by the platform 485, one of which is positioned adjacent each of the pivot supports 481 to maintain the pivot pins 441 in their proper position on the pivot supports 481 as illustrated. In this manner the rocker portion 440 is pivotal relative to the rocker support portion 481 regardless of the orientation of the device 1000, allowing the device 1000 to function regardless of its orientation in use.

A balance pad 442 and balancing cylinder 443 are formed at one end of the rocker arm 445 to counterbalance the weight of a cone-shaped air-flow closure member 447 and a pin 448 formed of a magnetically attractable material, such as stainless steel, both of which are carried at the opposite end of the rocker arm 445. Pin 448 is carried at one distal end of the rocker arm 445 between a plurality of gripping fingers 446 which encircle the pin 448 to hold the pin 448 in a position to be exposed to a magnetic field of a disc-shaped magnet 488 carried on the adjacent end of the air-flow tube 200 in a magnet holder 490. The disc-shaped magnet 488 and the pin 448 function to control or set the frequency of the PEP therapy oscillations and the expiratory air pressure required from the patient for this respiratory therapy.

In operation the cone-shaped air-flow closure member or air-flow closure cone 447 is sized and positioned on the rocker arm 445 to be periodically inserted into a tapered bell-shaped or trumpet-shaped air-discharge outlet 487 formed in the platform 485 to create a non-linear expiratory air discharge opening or outlet to create the oscillatory PEP when expiratory air is discharged through the air-flow tube discharge opening 203. As best illustrated in FIGS. 6 & 10, the interior of the air-discharge outlet 487 has a non-linear taper or bell-shaped interior to form the non-linear air discharge outlet for creating the oscillatory PEP therapy in response to the pivotal movement of the air-flow closure cone 447 in to and out therefrom. In this manner the discharge outlet 487 is periodically closed and re-opened in response to the patients expiratory air discharge allowing the oscillatory PEP therapy treatment.

The oscillatory rocker assembly 400 is secured onto the air-flow tube 200 and positioned within the housing 300 by means of a cowling 489 which extends downwardly from beneath the platform 485 encircling the exterior of the air-discharge outlet 487 to encircle and engage onto the outwardly extending circular outer sidewalls 287 of the air-flow tube discharge opening 203 as best illustrated in FIGS. 4 and 7. A pair of side walls 486 of the platform 485, the bottoms of which rest on the planar surface 205 of the air-flow tube 200, are formed with a ridged finger-engaging surface to facilitate the removal and repositioning of the rocker support portion 480 onto the air-flow tube 200 for cleaning the device 1000 as necessary. Sidewalls 486 extend vertically outward from the planar surface 205 of the air-flow tube 200 and are spaced apart a distance sufficient to receive the rocker arm 445 there between. In this manner the rocker arm 445 is protected between the sidewalls 486 when the upper and lower housing portions, 301 and 302, respectively, are separated for cleaning. This positioning protects the rocker assembly 400 from being inadvertently improperly grasped by a user or clinician when disassembling the device 1000 for cleaning, as the user's attention is directed to the ribbed or ridged finger-engaging surface of the side walls 486 which are intended to be grasped when the rocker assembly 400 is to be removed. A tang 384 extends downwardly from the interior of the upper housing portion 301, passing through an opening 444 formed in the rocker arm 445, to engage the upper surface 205 of the platform 485 to retain these components in the proper position regardless of the orientation of the device 1000 when in use.

The upper and lower housing portions, 301 and 302, respectively, are formed as two separable portions to facilitate access into the interior of the device for cleaning. To this end, the upper housing portion 301 is formed with a pair of tabs 303 at each end designed to engage complementary recesses 306 formed in the lower housing portion 302 to maintain the two portions of the housing 300 engaged unless it is desired to open the housing 300 for access to the interior thereof. When it is desired to open the housing 300, the sides of the upper housing 301 are compressed towards each other to facilitate release of the tabs 303 from the engaging recesses 306. A securing tab 305 extends outwardly from one end of the upper housing portion 301 in a position to engage a complementary recess 307 formed in the upper housing portion 301 adjacent to the patient coupling port 201 to facilitate securing the two housing portions together. The joinder of the securing tab 305 into the complementary recess 307 creates an outer diameter of a size for receiving the distal end of a standard mouthpiece 3 or mask 2 to prevent the inadvertent separation of the housing portions 301 and 302 when such components have been installed on the device 1000 when in use.

To control or set the desired frequency and/or expiratory pressure for the administration of the oscillatory PEP therapy, the magnetically attractable pin 441 is positioned on the rocker arm 445 within the magnetic field of the disc magnet 488. The disc magnet 488 is carried in a holder 490 which is slidably positionable in a vertical direction along a pair of vertically extending guides 210 which extend upwardly from the planar surface 205 of the air-flow tube 200 adjacent to the patient coupling port 201 in accordance with the rotational position of the frequency control dial 350. In this manner the desired frequency and/or expiratory pressure can be readily set or controlled by the user in accordance with the clinician's instructions.

The disc magnet 488 is carried in the holder 490 in a receiver pocket 491, and has a plurality of gripping or centering fingers 492 for retaining the magnet 488 in the circular-shaped receiver pocket 491. The receiver pocket 491 is formed at one end of the holder 490 and is movable in a vertical direction along the guides 210. The bottom of the holder is formed with a plurality of stops or feet 494 spaced from the bottom of the receiver pocket 491 for engaging therebetween a lip portion 395 of a cam 396 formed on the rotatable frequency control dial 350 carried in a horizontal position about the discharge opening 203 of the air-flow tube 200. In this manner the disc magnet 488 can be selectively positioned by the device user in operative proximity to the steel pin 448 to control or set the oscillatory frequency and/or expiratory air pressure desired for administering the oscillatory PEP therapy in accordance with the instructions of the clinician.

Referring to FIGS. 2, 8 and 10-13, the rotatable frequency control dial 350 and the cam 396 formed thereon are positioned concentrically about the sidewalls 287 of the air-flow tube discharge opening 203 by a plurality of guides 351. The inner diameter of the rotatable frequency control dial 350 is sized such that the dial 350 is freely rotatable while the guides 351 maintain the dial concentric with the sidewalls 287. The cam 396 is positioned such that the lip portion 395 thereof engages the magnet holder 490 between the bottom of the disc magnet receiver 491 and the stops or feet 494 so that the holder 490 is raised or lowered in accordance with the rotational position of the frequency control dial 350. In this manner the intensity of the magnetic field of the disc magnet 488 relative to the steel pin 448 carried by the rocker arm 445 will be varied there between as determined by the spacing between these components to provide an adjustable range of expiratory air pressure to be set for the creation of the oscillatory expiratory air pressure pulses.

To assist a user or the health care provider in using the device 1000, once the proper magnetic field strength has been established, a plurality of indicia 310 spaced along the frequency control dial 350 can be used to readily relocate the proper positioning. In addition, to maintain the proper positioning once the position has been determined, a series of detents 352 are utilized to prevent the inadvertent rotation of the dial 350. To this end a collar 510 supported from beneath the platform 485 encircles the upper portion of the sidewalls 287 of the air-flow tube discharge opening 203 and includes a projection 512 which sequentially engages the detents 352 to prevent inadvertent rotation of the frequency control dial 350. A recess 514 is engaged by a tab 414 extending downwardly from the bottom of platform 485 to hold collar 510 in the desired position.

In use, a patient discharges expiratory air through the patient coupling port 201 of the air-flow tube 200 which passes through the air-flow tube discharge opening 203 to the oscillatory rocker assembly 400 and then out of the device 1000 through the exit space 304 between the two housing portions 301 and 302. Accordingly, the expiratory air pressure is applied against the cone-shaped closure 447 of the rocker 445 which forms a closure of the non-linear discharge opening or orifice 487. The pressure of the patient's expiratory air will raise the cone-shaped closure 447, causing the rocker portion 440 to pivot about the pivot pins 441 against the force of the magnetic field between the disc magnet 488 carried on the pivotal rocker support portion 480 and the steel pin 448 carried on the rocker assembly 400. As the cone-shaped closure 447 moves upwardly in response to the increasing expiratory air pressure, the constant taper of the conical shape of the cone-shaped closure 447 in combination with the bell-shaped or trumpet-shaped non-linear taper discharge opening 487 forms a non-linear discharge orifice which increases in effective discharge area thereby decreasing the air pressure applied against the cone-shaped closure 447 and reducing the upward acceleration of the rocker arm 445.

When the magnetic force and the air flow over the bell-shaped or non-linear tapered interior surface of the discharge outlet 487 overcome the expiratory air pressure applied to the tapered cone-shaped closure 447, the cone-shaped closure 447 will again begin to move downwardly and accelerate into the bell-shaped non-linear tapered discharge orifice 487. As the cone descends into the air flow path through the discharge outlet or orifice 487, the annular flow area diminishes reducing the airflow rate and increasing the air pressure. This continues until the downward momentum is overcome, and the cone 447 resumes its upward acceleration. Maximum pressure is obtained at this point, and another cycle begins.

Selection of the proper resistance range produces the desired inspiratory air to expiratory air ratio (I:E) of about 1:3 to about 1:4.

The foregoing description of a preferred embodiment of this invention has been presented for purposes of illustration and description. It is not intended to be exhaustive or to limit the invention to the precise form disclosed. Obvious modifications or variations are possible in light of the above teachings. The embodiment was chosen and described in an effort to provide the best illustrations of the principles of the invention and its practical application, the best mode presently known to the inventors, to thereby enable one of ordinary skill in the art to utilize the invention in various embodiments and with various modifications as are suited to the particular use contemplated. All such modifications and variations are within the scope of the invention as determined by the appended claims as interpreted in accordance with the breadth to which they are entitled.

Also, this application was prepared without reference to any particular dictionary. Accordingly, the definition of the terms used herein conforms to the meaning intended by the inventors acting as their own lexicographer, in accordance with the teaching of the application, rather than any dictionary meaning which is contrary to or different from the inventors' meaning regardless of the authoritativeness of such dictionary.

What is claimed is:

1. An oscillatory positive expiratory pressure therapy device comprising:

an air-flow tube having a path of air flow movement from an inlet opening for receiving expiratory air passed thereto by a user receiving respiratory therapy, through an outlet opening for discharging the expiratory air passed through said inlet opening;

said air-flow tube including expiratory air responsive closure means positioned in said path of air flow movement and actuable between an open position and a closed position in response to the pressure of expiratory air passed thereto;

said expiratory air responsive closure means including a normally closed non-linear discharge outlet which is opened in response to the presence of a predeterminded pressure of expiratory air being passed in said path of air flow movement, and which closes in response to a predetermined rate of air pressure decrease through said non-linear discharge opening;

said expiratory air responsive closure means further including a closure member movable in response to the expiratory air in said path of air flow movement between a closed position blocking the flow of expiratory air and an open positions permitting the flow of expiratory air in said path of air flow movement wherein said closure member is cone-shaped and said non-linear discharge outlet is bell-shaped; and nebulizer coupling means for connecting a nebulizer into fluid communication with said air-flow path from said inlet opening to a user;

said nebulizer coupling means being formed in said air-flow tube in fluid communication between said inlet opening into said air-flow tube through which inspiratory air is received there into and said outlet opening for discharging expiratory air.

2. An oscillatory positive expiratory pressure therapy device, comprising:

an air-flow tube having a path of air flow movement from an inlet opening for receiving expiratory air passed thereto by a user receiving respiratory therapy, through an outlet opening for discharging the expiratory air passed through said inlet opening;

said air-flow tube including expiratory air responsive closure means positioned in said path of air flow movement and actuable between an open position and a closed position in response to the pressure of expiratory air passed thereto;

said expiratory air responsive closure means including a normally closed non-linear discharge outlet which is opened in response to the presence of a predetermined pressure of expiratory air being passed in said path of air flow movement, and which closes in response to a predetermined rate of air pressure decrease through said non-linear discharge opening;

said expiratory air responsive closure means further including a closure member movable in response to expiratory air in said path of air flow movement between a closed position blocking the flow of expiratory air and an open positions permitting the flow of expiratory air in said path of air flow movement;

nebulizer coupling means for connecting a nebulizer into fluid communication with said air-flow path from said inlet opening to a user;

a magnetic force field applying means for generating a biasing force effecting the opening and closing of said non-linear discharge opening including means for adjusting the magnitude of the magnetic force field applying means; and said means for adjusting the magnitude of the magnetic field applying means including a rotatable frequency control dial horizontally disposed relative to said non-linear discharge opening.

3. The oscillatory positive expiratory pressure therapy device of claim 2 wherein said rotatable frequency control dial further includes a plurality of circumferentially spaced detents for inhibiting the free rotation thereof.

4. The oscillatory positive expiratory pressure therapy device of claim 2 wherein said non-linear discharge outlet is bell-shaped.

* * * * *